(12) United States Patent
Bergonzelli et al.

(10) Patent No.: US 8,343,482 B2
(45) Date of Patent: Jan. 1, 2013

(54) BIFIDOBACTERIUM LONGUM AND HIPPOCAMPAL BDNF EXPRESSION

(75) Inventors: Gabriela Bergonzelli, Bussigny (CH); Kurt Ornstein, Savigny (CH); Christine Cherbut, Pully (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 12/937,866

(22) PCT Filed: Apr. 8, 2009

(86) PCT No.: PCT/EP2009/054199
§ 371 (c)(1),
(2), (4) Date: Jan. 7, 2011

(87) PCT Pub. No.: WO2009/127566
PCT Pub. Date: Oct. 22, 2009

(65) Prior Publication Data
US 2011/0280837 A1 Nov. 17, 2011

(30) Foreign Application Priority Data

Apr. 15, 2008 (EP) .................................... 08154550

(51) Int. Cl.
*A01N 63/00* (2006.01)
*A23K 1/18* (2006.01)
*A23L 1/28* (2006.01)
*A23C 9/12* (2006.01)

(52) U.S. Cl. ............. 424/93.3; 424/93.4; 426/2; 426/61

(58) Field of Classification Search ........................ None
See application file for complete search history.

(56) References Cited

U.S. PATENT DOCUMENTS

2004/0265279 A1* 12/2004 Dinan et al. ................. 424/93.4

FOREIGN PATENT DOCUMENTS

| JP | 2008081434 | 4/2008 |
| WO | WO 96/11014 | 4/1996 |
| WO | WO 2004/098622 | 11/2004 |
| WO | WO 2007/093619 | 8/2007 |

OTHER PUBLICATIONS

International Search Report for International Application No. PCT/EP2009/054199 mailed on Jul. 1, 2009.
Written Opinion for International Application No. PCT/EP2009/054199 mailed on Jul. 1, 2009.
M. Chao, et al., "Neurotrophin signalling in health and disease," Clinical Science, (2006), vol. 110, pp. 167-173.
A. Logan, et al., "Major depressive disorder: probiotics may be an adjuvant therapy," Medical Hypotheses, Eden Press, vol. 64, Issue 3, Jan. 1, 2005, pp. 533-538, XP004691105.

* cited by examiner

*Primary Examiner* — Chris R Tate
*Assistant Examiner* — Douglas F White
(74) *Attorney, Agent, or Firm* — K&L Gates LLP (57) ABSTRACT

The present invention relates in general to edible compositions comprising probiotics. One embodiment of the present invention relates to an edible composition comprising *Bifidobacterium longum* ATCC BAA-999. This composition can be used to attenuate reductions in hippocampal BDNF expression and/or to treat or prevent anxiety and related disorders.

1 Claim, 7 Drawing Sheets

FIG. 2

FIG. 3
Colonic inflammation

☐ Uninfected ▦ Tm-medium ▨ Tm-L. rhamnosus ▧ Tm-B. longum

FIG. 7
Anxiety-like behaviour step down test

FIG. 8

1: latency to re-enter bright box
2: total time spent in bright box (from re-entry)
3: number of crossings

BIFIDOBACTERIUM LONGUM AND HIPPOCAMPAL BDNF EXPRESSION

The present invention relates in general to edible compositions comprising probiotics. More particularly the present invention relates to edible compositions comprising *Bifidobacterium longum* ATCC BAA-999, and their use to increase hippocampal BDNF expression and/or to treat or prevent anxiety and related disorders.

Anxiety disorders affect about 40 million American adults of the age of 18 years and older. This represents on average about 18% of the adult population. A brief period of anxiety can be caused by for example by stressful events such as examinations or circumstances that are considered as slightly embarrassing. Anxiety can, however, last much longer, such as at least half a year, and the anxiety conditions can continue to become more severe and crippling if not treated. Anxiety disorders may also occur along with other mental or physical illnesses, including alcohol or substance abuse. Typical anxiety disorders are panic disorder, obsessive-compulsive disorder (OCD), post-traumatic stress disorder (PTSD), social phobia (or social anxiety disorder), specific phobias, and generalized anxiety disorder (GAD).

Some therapies for anxiety related disorders are available today. In general, anxiety disorders are treated with medication such as antidepressants, anti-anxiety drugs, or beta-blockers.

The medications alter brain chemistry, and sometimes have severe side effects. They can also have undesirable interactions with frequently taken medications.

Selective serotonin reuptake inhibitors, (SSRIs) alter the levels of the neurotransmitter serotonin in the brain supporting the communication of brain cells. SSRIs have fewer side effects than older antidepressants, but they sometimes produce slight nausea or jitters when people first start to take them. Some people also experience sexual dysfunction with SSRIs.

Tricyclics as antidepressants sometimes cause dizziness, drowsiness, dry mouth, and weight gain.

Monoamine oxidase inhibitors (MAOIs) are the oldest class of antidepressant medications. People who take MAOIs cannot eat a variety of foods and beverages (including cheese and red wine) that contain tyramine or take certain medications. They can also interact with caffeine. MAOIs can also cause confusion, hallucinations, increased sweating, muscle stiffness, seizures, changes in blood pressure or heart rhythm, and other potentially life-threatening conditions.

Benzodiazepines may cause drowsiness and patients may get used to them. Withdrawal symptoms are often reported after cessation of benzodiazepines. They also increase food intake and impair memory.

Beta-blockers can prevent the physical symptoms that accompany certain anxiety disorders, particularly social phobia.

All this medication may produce unwanted side-effects. Given the fact that a large amount of people is affected by anxiety related disorders, more or less severely, it would be desirable to have available a composition that can be safely administered without the risk of side effects.

WO2004098622 describes a method of treating depression comprising administering to a subject a bacterial strain.

The present inventors have however found that the effectiveness in treating and/or preventing anxiety, anxiety related disorders and/or neurodegenerative disorders depends on the bacterial genus, species and strain used.

Consequently, it was the object of the present invention to improve the state of the art and in particular to provide the art with a composition comprising a bacterial strain that is effective, readily available, low priced and safe to administer without unwanted side effects which can be used to treat or prevent disorders linked to a low hippocampal BDNF expression, such as anxiety, anxiety related disorders or neurodegenerative disorders.

The present inventors have addressed this need. They were surprised to see that they could achieve this object by the subject matter of the independent claims. The dependant claims further develop the idea of the present invention.

Consequently, one embodiment of the present invention is an edible composition comprising *Bifidobacterium longum*, in particular *Bifidobacterium longum* ATCC BAA-999. *Bifidobacterium longum* ATCC BAA-999 is commercially available.

*Bifidobacterium longum* ATCC BAA-999 (BL999) may for example be obtained from Morinaga Milk Industry Co. Ltd. of Japan under the trade mark BB536. It may be cultured according to any suitable method and prepared for encapsulation or for addition to products in a freeze-dried or spray-dried form for example.

While the present invention is disclosed with reference to the preferred *Bifidobacterium longum* strain, *Bifidobacterium longum* ATCC BAA-999, it should be understood, that the disclosure applies equally to the species *Bifidobacterium longum* in general.

*Bifidobacterium longum* ATCC BAA-999 was found to be in particular effective.

"Edible" means a material that is approved for human or animal consumption.

The term "*Bifidobacterium longum* ATCC BAA-999" is meant to include the bacterium, parts of the bacterium and/or a growth medium fermented by the bacterium.

The edible composition may be a medicament but is preferably a food composition, a pet food composition, a dietary supplement, a nutraceutical and/or a drink.

If the composition of the present invention is a food composition, this has the advantage that such a composition can be distributed in pharmacies, drug stores, but also in normal supermarkets, where the compositions are easily available to everybody.

The generally pleasant taste of food compositions will further contribute to the acceptance of the product. In particular small children or pets are much more likely to readily consume compositions with a taste that is generally liked.

Examples of food products that are applicable to the present invention are yoghurts, milk, flavoured milk, ice cream, ready to eat desserts, powders for re-constitution with, e.g., milk or water, chocolate milk drinks, malt drinks, ready-to-eat dishes, instant dishes or drinks for humans or food compositions representing a complete or a partial diet intended for pets or livestock.

Consequently, in one embodiment the composition according to the present invention 15, is a food product intended for humans, pets or livestock. In particular the composition is intended for animals selected from the group consisting of dogs, cats, pigs, cattle, horses, goats, sheep, poultry or humans, and in a preferred embodiment is the composition a food product intended for adult species, in particular human adults.

The composition of the present invention may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, antioxidants and antimicrobials. The composition may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like. In all cases, such further components will be selected having regard to their suitability for the intended recipient.

The composition may be a nutritionally complete formula.

The composition according to the invention may comprise a source of protein.

Any suitable dietary protein may be used, for example animal proteins (such as milk proteins, meat proteins and egg proteins); vegetable proteins (such as soy protein, wheat protein, rice protein, and pea protein); mixtures of free amino acids; or combinations thereof. Milk proteins such as casein and whey, and soy proteins are particularly preferred.

The proteins may be intact or hydrolysed or a mixture of intact and hydrolysed proteins. It may be desirable to supply partially hydrolysed proteins (degree of hydrolysis between 2 and 20%), for example for human subjects and/or animals at risk of developing cows' milk allergy. If hydrolysed proteins are required, the hydrolysis process may be carried out as desired and as is known in the art. For example, a whey protein hydrolysate may be prepared by enzymatically hydrolysing the whey fraction in one or more steps. If the whey friction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

The composition may also contain a source of carbohydrates and a source of fat.

If the composition includes a fat source, the fat source preferably provides 5% to 40% of the energy of the composition; for example 20% to 30% of the energy. A suitable fat profile may be obtained using a blend of canola oil, corn oil and high-oleic acid sunflower oil.

A source of carbohydrate may be added to the composition.

The source of carbohydrates preferably provides 40% to 80% of the energy of the composition. Any suitable carbohydrate may be used, for example sucrose, lactose, glucose, fructose, corn syrup solids, maltodextrins, and mixtures thereof. Dietary fibre may also be added if desired. Dietary fibre passes through the small intestine undigested by enzymes and functions as a natural bulking agent and laxative. Dietary fibre may be soluble or insoluble and in general a blend of the two types is preferred. Suitable sources of dietary fibre include soy, pea, oat, pectin, guar gum, partially hydrolysed guar gum, gum Arabic, fructooligosaccharides, acidic oligosaccharides, galacto-oligosaccharides, sialyl-lactose and oligosaccharides derived from animal milks. A preferred fibre blend is a mixture of inulin with shorter chain fructo-oligosaccharides. Preferably, if fibre is present, the fibre content is between 2 and 40 g/l of the composition as consumed, more preferably between 4 and 10 g/l.

The composition may also contain minerals and micronutrients such as trace elements and vitamins in accordance with the recommendations of Government bodies such as the USRDA. For example, the composition may contain per daily dose one or more of the following micronutrients in the ranges given: —300 to 500 mg calcium, 50 to 100 mg magnesium, 150 to 250 mg phosphorus, 5 to 20 mg iron, 1 to 7 mg zinc, 0.1 to 0.3 mg copper, 50 to 200 µg iodine, 5 to 15 µg selenium, 1000 to 3000 µg beta carotene, 10 to 80 mg Vitamin C, 1 to 2 mg Vitamin B1, 0.5 to 1.5 mg Vitamin B6, 0.5 to 2 mg Vitamin B2, 5 to 18 mg niacin, 0.5 to 2.0 µg Vitamin B12, 100 to 800 µg folic acid, 30 to 70 µg biotin, 1 to 5 µg Vitamin D, 3 to 10 µg Vitamin E.

One or more food grade emulsifiers may be incorporated into the composition if desired; for example diacetyl tartaric acid esters of mono- and di-glycerides, lecithin and mono- and di-glycerides. Similarly suitable salts and stabilisers may be included.

The composition is preferably orally or enterally administrable; for example in the form of a powder for re-constitution with milk or water.

According to one preferred embodiment of the present invention the composition comprises at least one other kind of other food grade micro-organism.

"Food grade" micro-organisms are micro-organisms that are safe for use in food.

The food grade micro-organisms are preferably food-grade bacteria or food-grade yeast. The food grade bacteria may be selected from the group consisting of lactic acid bacteria, bifidobacteria, propionibacteria or mixtures thereof. As food grade yeast for example *Saccharomyces cerevisiae* and/or *Saccharomyces boulardii* can be used.

The food grade bacteria may be probiotic bacteria.

"Probiotic" means microbial cell preparations or components of microbial cells with a beneficial effect on the health or well-being of the host. (Salminen S, Ouwehand A. Benno Y. et al "Probiotics: how should they be defined" Trends Food Sci. Technol. 1999:10 107-10).

Probiotic bacteria are preferably selected from the group consisting of lactic acid bacteria, bifidobacteria, propionibacteria or mixtures thereof. Probiotic bacteria may be any lactic acid bacteria or bifidobacteria with established probiotic characteristics. For example they may be also capable of promoting the development of a bifidogenic intestinal microbiota.

Suitable probiotics may be selected from the group consisting of *Bifidobacterium, Lactobacillus, Streptococcus* and *Saccharomyces* or mixtures thereof, in particular selected from the group consisting of *Bifidobacterium longum, Bifidobacterium lactis, Lactobacillus acidophilus, Lactobacillus rhamnosus, Lactobacillus paracasei, Lactobacillus johnsonii, Lactobacillus plantarum, Lactobacillus salivarius, Enterococcus faecium, Saccharomyces boulardii* and *Lactobacillus reuteri* or mixtures thereof, preferably selected from the group consisting of *Lactobacillus johnsonii* (NCC533; CNCM I-1225), *Bifidobacterium longum* (NCC490; CNCM I-2170), *Bifidobacterium longum* (NCC2705; CNCM I-2618), *Bifidobacterium* lactis (2818; CNCM I-3446), *Lactobacillus paracasei* (NCC2461; CNCM I-2116), *Lactobacillus rhamnosus* GG (ATCC53103), *Lactobacillus* rhamnosus (NCC4007; CGMCC 1.3724), *Enterococcus faecium* SF 68 (NCIMB10415), and mixtures thereof.

In a preferred embodiment of the present invention the composition further contains at least one prebiotic. "Prebiotic" means food substances intended to promote the growth of probiotic bacteria in the intestines.

Prebiotics can thus promote the growth of certain food grade bacteria, in particular of probiotic bacteria, in the intestines and can hence enhance the effect of *Bifidobacterium longum* ATCC BAA-999. Furthermore, several prebiotics have a positive influence on, e.g., digestion.

Preferably the prebiotic is selected from the group consisting of oligosaccharides and optionally contain fructose, galactose, mannose, soy and/or inulin; dietary fibers; or mixtures thereof.

The *Bifidobacterium longum* ATCC BAA-999, may be used, both, as living bacterium as well as inactivated bacterial species.

It is preferred that at least a part of the *Bifidobacterium longum* ATCC BAA-999, are alive in the composition and preferably arrive alive in the intestine. This way they can persist in the intestine and may increase their effectiveness by multiplication. They may also be effective by interacting with the commensal bacteria and/or the host.

For special sterile food products or medicaments, for example it might be preferable that *Bifidobacterium longum* ATCC BAA-999, is not alive in the composition. Hence, in one embodiment of the present invention at least a part of the *Bifidobacterium longum* ATCC BAA-999, are not alive in the composition.

*Bifidobacterium longum* ATCC BAA-999, will be effective in any concentration.

For the composition of the present invention it is generally preferred that a daily dose of the composition comprises between $10^4$ and $10^{12}$ cfu (colony forming units) of *Bifidobacterium longum* ATCC BAA-999. A particular suitable daily dose of *Bifidobacterium longum* ATCC BAA-999, is from $10^5$ to $10^{11}$ cfu, more preferably from $10^7$ to $10^{10}$ cfu.

The composition of the present invention may also comprise between $10^2$ and $10^{10}$ cfu, preferably $10^3$ to $10^8$ colony forming units, more preferably from $10^5$ to $10^8$ cfu of *Bifidobacterium longum* ATCC BAA-999, per gram dry weight of the composition.

In the case of inactivated *Bifidobacterium longum* ATCC BAA-999, it is generally preferred that the composition of the present invention comprises between $10^2$ and $10^{10}$ non-replicating cells of *Bifidobacterium longum* ATCC BAA-999, per gram of the dry weight of the composition. A particular suitable dose of *Bifidobacterium longum* ATCC BAA-999, is from $10^3$ to $10^8$ non-replicating cells, more preferably from $10^5$ to $10^8$ non-replicating cells per gram of the dry weight of the composition.

The present inventors were in particular surprised to find that the composition of the present invention can successfully be used to significantly increase hippocampal BDNF expression.

BDNF (Brain-derived neurotrophic factor) is a growth factor from a unique family of polypeptide growth factors that influence proliferation, differentiation, survival and death of neuronal and non-neuronal cells. BDNF and the other neurotrophic factors, e.g., NGF (nerve growth factor), NT-3 (neurotrophin-3), and NT-4 (neurotrophin-4) are essential for the health and well-being of the nervous system, and mediate higher-order activities such as learning, memory, behaviour in addition to their role in cell survival. Alterations of the neurotrophin levels have been implicated in neurodegenerative disorders, such as Alzheimer's, Huntington's and Parkinson's disease, as well as in psychiatric disorders including depression and abuse of substances (Chao et al., 2006, Clin. Sci., 110:167-173).

One embodiment of the present invention is consequently the edible composition comprising *Bifidobacterium longum* ATCC BAA-999, and/or its growth medium to increase hippocampal BDNF expression.

The present invention also relates to the use of the composition described above for the preparation of a formulation to increase hippocampal BDNF expression.

*Bifidobacterium longum* ATCC BAA-999, and/or the composition of the present invention may consequently be used to treat or prevent disorders linked to a decreased hippocampal BDNF expression. Administering an effective dose of *Bifidobacterium longum* ATCC BAA-999, will also help to attenuate a decrease in hippocampal BDNF expression.

The composition of the present invention may consequently be used to treat or prevent anxiety, and/or anxiety related disorders as well as their symptoms. It may also be used to treat or prevent neurodegenerative diseases.

The anxiety related disorder may be selected from the group consisting of depression, abuse of substances, such as alcohol abuse, cocaine abuse, opiate abuse, compulsive eating, and deleterious effects of stress such as sleep disturbances and cognitive impairments.

Neurodegenerative diseases are preferably selected from the group consisting of Alzheimer's, Parkinson's, Huntington's disease, brain inflammation and diabetes.

Importantly, the subject matter of the present invention may also be used to improve brain performance, in particular in elderly people and/or during ageing.

Notably, *Bifidobacterium longum* ATCC BAA-999, and/or the composition of the present invention may also be used to reduce the amount of medication needed to treat or prevent disorders linked to a decreased hippocampal BDNF expression.

It is clear to those skilled in the art that any features described in this specification can be combined freely without departing from the scope of the present invention as disclosed. In particular, all features described for the composition of the present invention are applicable to the use of the present invention and vice versa.

FURTHER FEATURES AND ADVANTAGES OF THE PRESENT INVENTION RESULT FROM THE following EXAMPLES AND FIGURES

EXAMPLES

Figure 1:
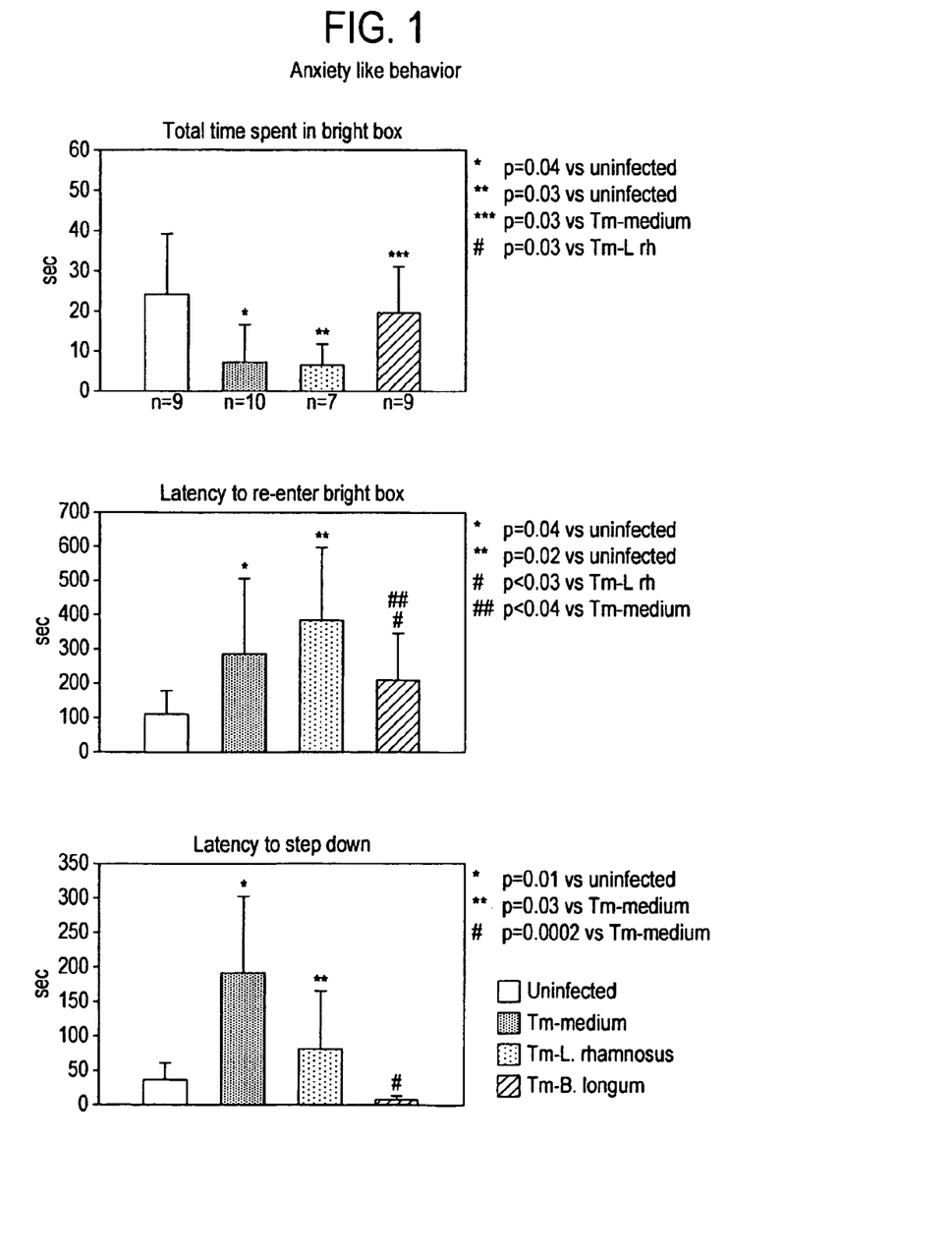
FIG. 1 shows the result of a black box/bright box test: total time spent in bright box and latency to re-enter bright box and of a step down test in mice infected with *Trichuris muris* (Tm). Tm-medium and Tm-*B. longum* are Tm infected mice treated with fresh medium (negative control) and *Bifidobacterium longum* ATCC BAA-999, respectively; a Tm group treated with *L. rhamnosus* (L. rh) strain is shown for comparison.
Figure 2:
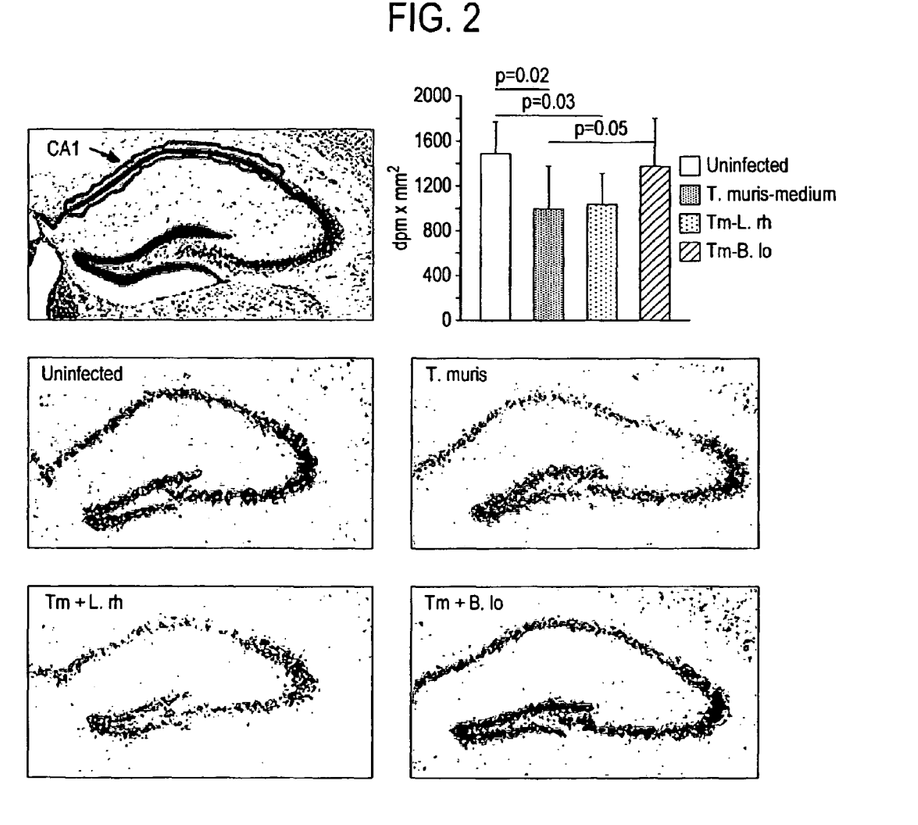
FIG. 2 shows the results of the in situ hybridization in the brain hippocampal region of mice infected with a *Trichuris muris* (Tm). Tm-*B. longum* is Tm infected mice treated with *Bifidobacterium longum* ATCC BAA-999; a Tm group of mice treated with *L. rhamnosus* strain is shown for comparison. Quantification of $^{35}S$ signals was performed by autoradiography and image analysis (right upper panel).
Figure 3:
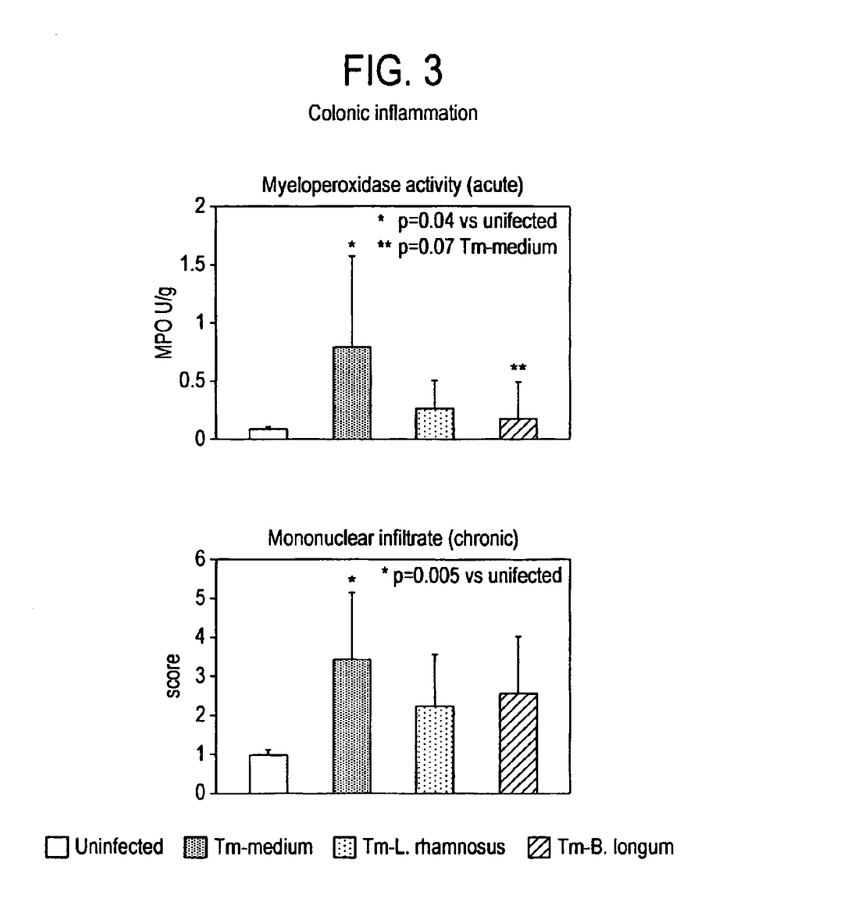
FIG. 3 shows the results obtained on colonic inflammation measured by myeloperoxidase activity assay (left panel) and mononuclear cell infiltration (right panel) in mice infected with *Trichuris muris* (Tm). Tm-medium and Tm-*B. longum* are Tm infected mice treated with fresh medium (negative control) and *Bifidobacterium longum* ATCC BAA-999; a Tm group of mice treated with *L. rhamnosus* strain is shown for comparison.

Mice chronically infected with the parasite Trichuris muris showed an increase in anxiety-like behaviour in two behavioural tests: 1) In the black box/bright box test, infected animals showed a decrease in the time spent in the bright box and an increase of the latency to re-enter the bright box; 2) In the step down test, the infection increased the latency to step down from the pedestal (FIG. 1). The effect on behaviour was correlated with a normalization of Trichuris muris-mediated decrease in BDNF levels in the hippocampus only observed in mice treated with B. longum (FIG. 2). In contrast, treatment with B. longum as well as with L. rhamnosus resulted in a reduction of myeloperoxidase activity and mononuclear infiltration previously induced by Trichuris muris infection (FIG. 3) indicating that the normalization of behaviour was independent of the anti-inflammatory effect of the bacteria.

Figure 4:
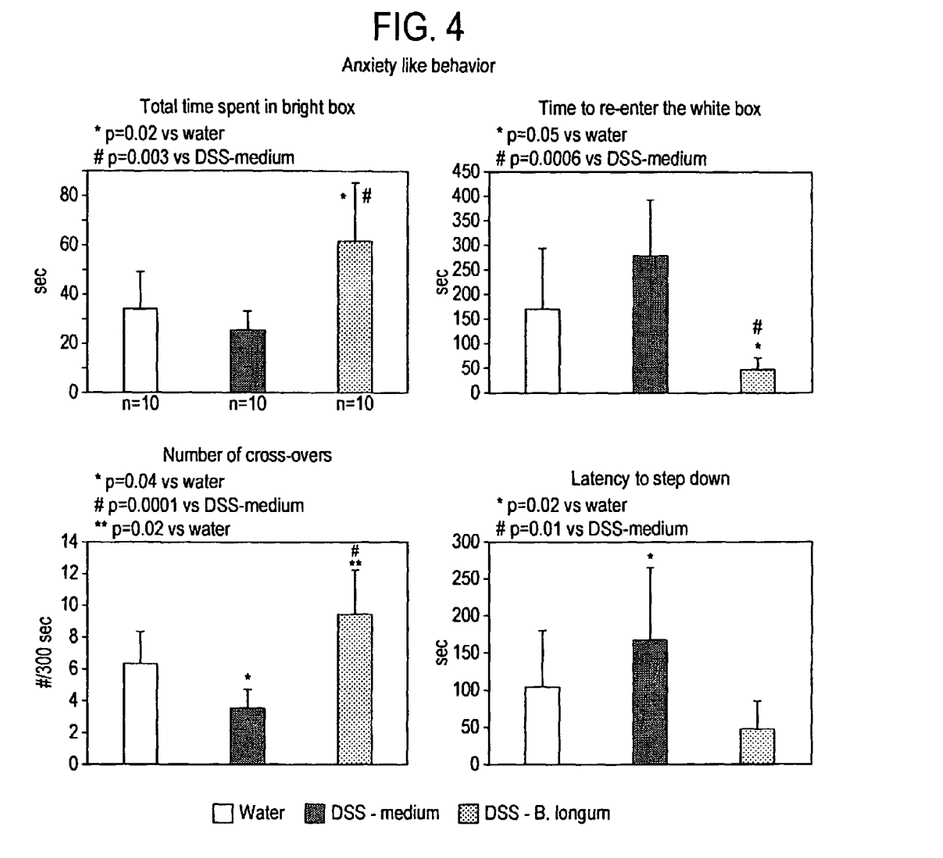
FIG. 4 shows the result of a black box/bright box test: total time spent in bright box and latency to re-enter bright box and of a step down test in mice with chronic DSS-induced colitis. DSS-medium and DSS-*B. longum* are mice with DSS-induced colitis treated with fresh medium (negative control) or *Bifidobacterium longum* ATCC BAA-999, respectively.
Figure 5:
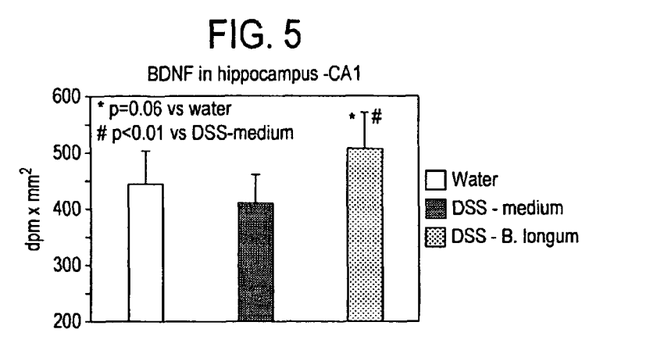
FIG. 5 shows the results of the in situ hybridization in the brain hippocampal region of mice with chronic DSS-induced colitis. DSS-medium and DSS-B. longum are mice with DSS-induced colitis treated with fresh medium (negative control) or Bifidobacterium longum ATCC BAA-999, respectively. Quantification of $^{35}$S signals was performed by autoradiography and image analysis (right upper panel).
Figure 6:
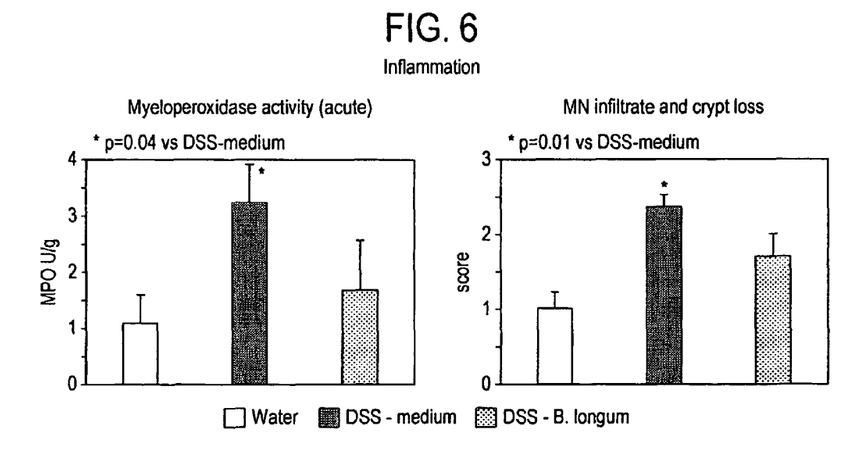
FIG. 6 shows the results obtained on colonic inflammation measured by myeloperoxidase activity assay (left panel) and mononuclear cell infiltration (right panel) in mice with chronic DSS-induced colitis. DSS-medium and DSS-B. longum are mice with DSS-induced colitis treated with treated with fresh medium (negative control) or Bifidobacterium longum ATCC BAA-999, respectively.

The effect of B. longum was confirmed in the mouse model of chronic DSS-induced colitis. Even if less important than the impact of Trichuris muris infection, DSS increased anxiety (FIG. 4) and tended to decrease BDNF levels in the hippocampus (FIG. 5). Treatment of DSS-mice with B. longum decreased anxiety even below the levels of control mice as evidenced in the black box/bright box test by an increase of the total time spent in the bright box and a decrease of the time to re-enter the bright box and the number of crossing (FIG. 4) and also by a reduction of the latency to step down from the pedestal observed in the step down test (FIG. 4). Furthermore, in accordance to the behavioural tests, treatment with B. longum increased BDNF levels in the hippocampus over the basal levels (FIG. 5). Similar to what observed in the model of Trichuris muris infection, B. longum diminished colonic inflammation (FIG. 6).

Figure 7:
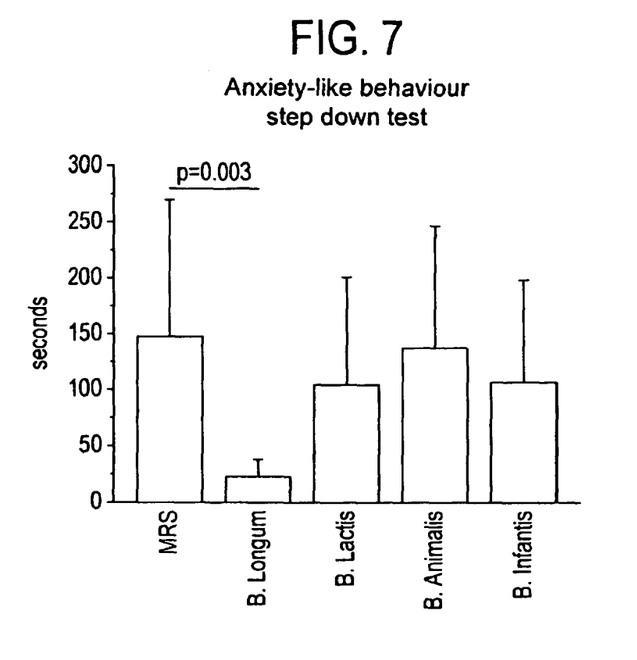
FIG. 7 shows the result of an anxiety-like behaviour test (step down test) performed in mice with chronic DSS-induced colitis and further treated with fresh medium (MRS, negative control) or with different Bifidobacterium species. The tested B. longum strain was Bifidobacterium longum ATCC BAA-999; the results obtained with B. lactis, B. animals and B. infantis strains are shown for comparison.

To determine whether the capacity of B. longum to normalize altered behaviour was common to other bifidobacteria, we measured the effect on behaviour of B. longum in parallel with three other Bifidobacterium species—one B. lactis, one B. animalis and one B. infantis—using the model of DSS-induced colitis and the step down test (FIG. 7). Apart of B. longum, none of the other Bifidobacterium species tested was able to the latency to step down from the pedestal clearly indicating that it is not possible to extrapolate this particular property of B. longum to other species of the genus Bifidobacterium.

Materials and Methods:
Bacterial Culture Conditions

Probiotics were grown under anaerobic conditions in Man-Rogosa-Sharpe (MRS, BioMerieux) broth (bifidobacteria with 0.5% cysteine). After 24 h at 37° C., the number of bacteria was estimated by measuring the optical density at 600 nm (1 OD600=$10^8$ bacteria/mL). Bacterial cells were pelleted by centrifugation at 5000×g for 15 min at 4° C. and further resuspended at a concentration of $10^{10}$/mL in their spent culture medium. Aliquots of 1 mL were kept frozen until use.

Animals

Male BALB/c or AKR mice (Harlan, Canada) were purchases at age of 6-8 wks and housed in a conventional specific pathogen free unit at McMaster University Central Animal Facility. All experiments were conducted with approval from the McMaster University Animal Care Committee.

Design

Figure 8:
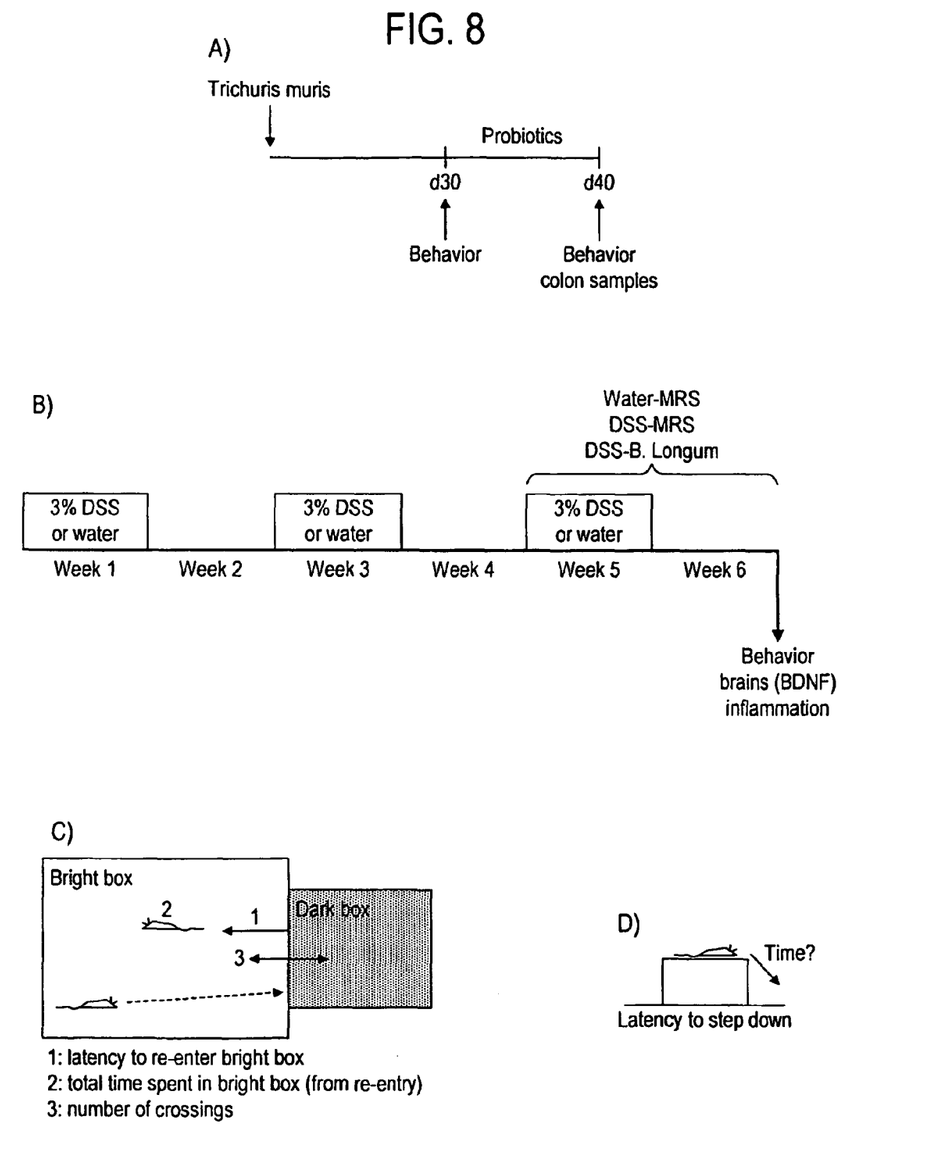
FIG. 8 shows a timeline for infection of male AKR mice with Trichuris muris, treatment of the infected mice with a probiotic such as L. rhamnosus or B. longum, assessment of anxiety behavior of the treated mice, and acquisition of colon samples from the treated mice (A); and a schedule for treatment of male AKR mice with three cycles of 3% dextran sodium sulphate (DSS) or water (control), followed by treatment with B. longum and DSS or MRS (control), assessment of anxiety behavior of the treated mice, and acquisition of brain samples from the treated mice (B). For both of the above timelines, anxiety behavior was assessed in the treated mice by a dark box/bright box test (C) or by a step-down test (D).

Chronic Trichuris muris Infection (see FIG. 8, panel A):

Male AKR mice were gavaged with T. muris (300 eggs/mouse) (n=26) or with placebo (n=9). Infected mice were then gavaged daily with L. rhamnosus, B. longum or fresh MRS from day 30 for 10 days. Uninfected mice were gavaged with fresh MRS on a daily basis from day 30 to day 40. At the end of probiotic or placebo administration, the mice underwent black box/white box and step-down tests. The mice were sacrificed thereafter and tissue samples were obtained. Colon samples were fixed in formalin for histological analysis or were snap frozen for MPO determination. Brains were snap frozen in liquid nitrogen and stored for in situ hybridization.

Chronic DSS Colitis (See FIG. 8, Panel B):

Male AKR mice (n=20) were treated with three cycles of 3% Dextran Sodium Sulphate (MP Biomedicals, Solon, Ohio, USA) (one cycle consists of 1 week of DSS followed by 1 week of wash-our period). Additional group of mice (n=10) received placebo-drinking water only. The infected mice were gavaged daily with B. longum or other Bifidobacteria for 2 weeks during the last cycle of DSS treatment. Control mice were gavaged daily with MRS for 2 weeks. At the end of probiotic or placebo administration, the mice underwent black box/white box and/or step-down tests. The mice were sacrificed thereafter and tissue samples were obtained. Colon samples were fixed in formalin for histological analysis or were snap frozen for MPO determination. Brains were snap frozen in liquid nitrogen and stored for in situ hybridization.

Behaviour Testing

Black Box/bright Box (See FIG. 8, Panel C):

Anxiety behaviour was assessed individually in mice using black box/white box as described in the literature. Briefly, each mouse was placed in the centre of an illuminated white box (30×30 cm) connected by an opening (10×3 cm) to smaller black box (30×15 cm). The locomotor behavior of each mouse in a white box was recorded for 10 min by a digital video camera and stored in a computer for an off-line analysis. Several parameters were assessed by a blinded observer including total time spent in white box, latency to re-enter white box (time spent in black box after first entry), and number of crossovers (number of crossing from black box to white box).

Step-down Test (See FIG. 8, Panel D):

Anxiety behaviour was assessed using step down test as described in the literature. Briefly, each mouse was placed in the centre of an elevated platform (7.5 cm in diameter, 3 cm high) positioned in the middle of a black floor. Latency to step down from the pedestal was measured by a stop-watch; maximum duration of the test was 5 min.

Histology

Colon samples were fixed in 10% formalin and then stained with hematoxylin-eosin. The slides were examined under light microscopy to grade for acute and chronic inflammatory infiltrate.

Myeloperoxidase Activity Assay

In order to assess acute intestinal inflammation, myeloperoxidase activity (MPO) assay was performed on frozen tissues as described previously. MPO activity is expressed in units per mg of tissue, where one unit of MPO is defined as a quantity of the enzyme able to convert 1 μmol of hydrogen peroxide to water in 1 minute at room temperature.

In Situ Hybridization in the CNS

Levels of BDNF in hippocampus were assessed by in situ hybridizations using $^{35}$S-labeled RNA probes on frozen brain sections as described previously (Whitfield et al., 1990; Foster et al., 2002). Briefly, brains were removed and rapidly frozen by immersion in 2-methylbutane at −60° C., and stored at −70° C. Cryostat-cut 12-μm-thick coronal sections were thaw-mounted onto gelatin-coated slides, dried, and stored at −35° C. Tissue sections were fixed with 4% formaldehyde, acetylated with 0.25% acetic anhydride in 0.1 M triethanolamine-HCl, pH 8.0, dehydrated, and delipidated with chloroform. Antisense BDNF ribonucleotide probe was transcribed from linearized plasmid using the Riboprobe System (Promega Biotech, Burlington, ON) with α-$^{35}$S-UTP (specific activity >1000 Ci/mmol; Perkin-Elmer, Boston, Mass.) and T3 and T7 polymerases respectively. Radiolabeled probes were diluted in a hybridization buffer (0.6 M NaCl, 10 mM Tris pH 8.0, 1 mM EDTA pH 8.0, 10% Dextran sulfate, 0.01% sheared salmon sperm DNA, 0.05% total yeast RNA, type XI, 0.01% yeast tRNA, 1×Denhardt's solution) and applied to brain sections (approximately 500,000 CPM/section). Slides were incubated overnight at 55° C. in a humidified chamber. To reduce nonspecific binding of the probe, slides were washed in 20 μg/ml RNase solution for 30 min at room temperature, followed by 1 h each in 2×SSC at 50° C., 0.2×SSC at 55° and 60° C. Slides were dehydrated and air-dried for autoadiography. Slides and $^{14}$C plastic standards were placed in x-ray cassettes, apposed to film (BioMax MR; Eastman Kodak, Rochester, N.Y.) for 5 days and developed (Kodak Medical X-Ray Processor). Autoradiographic film images of brain sections and standards were digitized with a solid-state camera with a 60 mm Nikon lens using QCapture software (Qicam; Quorum Technologies Inc., Guelph, ON) and a Macintosh computer-based image analysis system with Image software (http://rsb.info.nih.gov/nih-image). Light transmittance through the film was measured by outlining the structure on the monitor. For BDNF mRNA, transmittance was converted to radioactivity levels using the Rodbard curve applied to the standards.

The calculated DPM were then multiplied by area to produce a measurement of integrated density. Illustrations were made directly from the captured images.

Statistical Analysis

Data are presented as mean±standard deviation or medians with interquartile ranges as appropriate. Data was analysed using either two-way ANOVA, test or non-paired t-test as appropriate. A p value of <0.05 was considered as statistically significant.

The invention claimed is:

1. A method for treating anxiety and/or an anxiety related disorder comprising the step of administering an effective amount of *Bifidobacterium longum* ATCC BAA-999 to a patient having the same, wherein the anxiety related disorder is selected from the group consisting of depression, abuse of substances, compulsive eating, and deleterious effects of stress.

* * * * *